US006752331B2

(12) United States Patent
Wu

(10) Patent No.: US 6,752,331 B2
(45) Date of Patent: Jun. 22, 2004

(54) AIR-PRESSURE SPRAYER STRUCTURE

(75) Inventor: Jui-Chang Wu, Changhua Hsien (TW)

(73) Assignee: SK & Y Agricultural Equipments Co., Ltd. (TW)

( * ) Notice: Subject to any disclaimer, the term of this patent is extended or adjusted under 35 U.S.C. 154(b) by 155 days.

(21) Appl. No.: 10/123,177

(22) Filed: Apr. 17, 2002

(65) Prior Publication Data

US 2003/0197069 A1 Oct. 23, 2003

(51) Int. Cl.[7] .................................... A61M 11/02
(52) U.S. Cl. ..................... 239/373; 222/470; 222/518
(58) Field of Search ....................... 239/373; 222/470, 222/518

(56) References Cited

U.S. PATENT DOCUMENTS 2,091,735 A * 8/1937 Jepson ....................... 222/401
3,282,510 A * 11/1966 Van Schwartz ............. 239/373
4,537,334 A * 8/1985 Spengler et al. ............ 222/401

* cited by examiner

*Primary Examiner*—Dinh Q. Nguyen
(74) *Attorney, Agent, or Firm*—Bacon & Thomas, PLLC

(57) ABSTRACT

An air-pressure sprayer. The air-pressure sprayer includes a container, a cover unit, an air-pump unit, a spray mouthpiece unit, and a water-stop valve wherein the cover unit, screw jointed to said container, has a press body disposed at one side thereof which can control the movement of the water-stop valve located in parallel position at the other side thereof. The air-pump unit has a valve rod with a head knob disposed at the top and an air-relief valve attached at the bottom thereof. The valve rod and the air-relief valve are led through a sleeve cylinder and joined to the cover unit at the upper section. The spray mouthpiece unit, attached to one side of said cover unit via a sleeve body and a pivot body, can be moved upwards or downwards to point at different directions for use.

4 Claims, 8 Drawing Sheets

AIR-PRESSURE SPRAYER STRUCTURE

BACKGROUND OF THE INVENTION

The present invention is related to an improved air-pressure sprayer structure, comprising a container, a cover unit, an air-pump unit, a spray mouthpiece unit, and a water-stop valve wherein said cover unit, engaged with said water-stop valve at one side and said air-pump unit at the other side, is screw jointed to said container and attached to said spray mouthpiece unit for use. Said air-pump unit is provided with an air-relief valve through which extra air can be released when said container is saturated with air, preventing the danger of explosion due to over air pressure to achieve the purpose of safety.

Please refer to FIG. 1. A conventional air-pressure sprayer is made up of a container 10, a cover body 11, a water-outlet pipe 12, a press body 13, a water-stop valve 14, a locating means 15, a valve rod 16, a sleeve tube 17, and a spray nozzle 18. The container 10 is provided with outer threads 101 and a water opening 102 disposed at the upper section thereof A projected pivot slot 111 and a receiving groove 112 defined by said projected pivot slot 111 are disposed at the top face of the cover body 11. The receiving groove 112 is equipped with an indented locating slot 1121 at one side and a handle 113 at the other side. The cover body 11 is provided with a screw body 114 disposed at the opposite side of the handle 113 thereof to be engaged with the spray nozzle 18 having spray port 181 disposed at the center thereof via internal threads 182 disposed at one end thereof. A water-discharge hole 115 is disposed at the center of the screw body 114 at one end, connecting with a through hole 1151 at other end thereof via the water-outlet pipe 12 led through the passage there-between. The underside of the cover body 11 is provided with a screw fixing hole 116, extending downwards under the projected pivot slot 111, and internal threads with an anti-leak ring 118 disposed at the interior side thereof. The press body 13 comprises a locating slot 131 with an abutting part 132 having a blocking flange 132 disposed at the front thereof, and a locating hole 134 with a pair of locating posts 133 extending downwards at the front surface thereof.

The water-stop valve 14 has a water-stop part 141 disposed at one end, a water-outlet part 143 having an anti-leak washer 144 and a spring 142 sleeve jointed at the middle section thereof, and a fixing part 146 with a block body 145 disposed thereon at the other end thereof. The locating means 15 has a locating recess 151 disposed at one side with an abutting plate 152 disposed at the top thereof. The valve rod 16 comprises a knob 161 with a stop ring 162 disposed at the upper section, a rod body 163 disposed at the lower section with a valve body 165 having an anti-leak ring 164 disposed thereon being screwed to the bottom of the rod body 163. The sleeve tube 17 is provided with an anti-leak ring 172 and a projecting flange 173 with external threads section 171 disposed at the upper end thereof, and a through hole 175 circled by a multiple of air ports 174 at the bottom center thereof. A guard valve 176 having a fixing post 177 disposed thereon is attached to the bottom of the sleeve tube. 17 via the fixing post 177 thereof being inserted into said through hole 175 thereof.

Thus, a conventional air-pressure sprayer can be assembled by the parts and structure above as shown in FIG. 2. Please refer to FIG. 3. In operation, water is poured into said container 10 via said water opening 102. Said knob 161 of said valve rod 16 is then drawn up and down to pump air into said container 10. When said container 10 is saturated with air, said press body 13 is pushed downwards, pulling back said water-stop valve 14 hooked to said locating means 15 by the block body 145 thereof, and dislocating said water-stop part 141 of said water-stop valve 14 to move from the spray port 181 of said spray nozzle 18 for the air enclosed within said container 10 to escape therefrom. Meanwhile, water is bought out by the outflow air pressure, flowing through said pipe 12 to the water-discharge hole 115 thereof to be released from said spray nozzle 18 via said spray port 181 as shown in FIG. 3.

There are several drawbacks to such conventional air-pressure sprayer. First, without an air-relief valve, a saturated container like said container 10 can be easily exploded due to over air-pressure if said valve rod 16 keeps pumping in air. Second, said water-stop valve 14, aligned in a straight line with said press body 13, might reduce the pulling force due to the right-angle formed by the push-and-pull movement thereof, making said spring 142 easily worn out and thus resulting in the leak of both air and water. Third, said guard valve 176, simply joined to said sleeve tube 17, is easily distorted, causing the pumped-in air to flow back to said sleeve tube 17 and making said container 10 hard to retain sufficient air pressure for use. Fourth, said guard valve 176 is complicated, boosting the cost of production. Fifth, said spray nozzle 18 can only be pointed transversely at one direction, greatly limiting the range of use of said conventional air-pressure sprayer.

SUMMARY OF THE PRESENT INVENTION

It is, therefore, the primary purpose of the present invention to provide an improved air-pressure sprayer structure wherein, via the safety device of an air-relief valve, a saturated container will stop taking in more air if a valve rod keeps pumping in air, avoiding the danger of explosion due to over air-pressure for the purpose of safety.

It is, therefore, the second purpose of the present invention to provide an improved air-pressure sprayer structure wherein a slide block is applied to locate a press body in an attitude of constant spraying without interruption. Moreover, the force applied onto said press body is parallel to the movement of a water-stop valve to reach a balance of forces in operation, preventing the distortion of said water-stop valve and the leak of both air and water.

It is, therefore, the third purpose of the present invention to provide an improved air-pressure sprayer structure wherein when the container is saturated with air, a valve guard member will be pressed by air-pressure to abut tightly against the bottom of a sleeve part, avoiding the pumped-in air to escape from the container. Moreover, said valve guard member is abutted against a pair of protecting arms disposed at the bottom of said sleeve part, preventing the distortion of said valve guard member and effectively retaining air-pressure within the container for use.

It is, therefore, the fourth purpose of the present invention to provide an improved air-pressure sprayer structure wherein said valve guard member is easily and quickly made, economically saving the time and cost of production.

It is, therefore, the fifth purpose of the present invention to provide an improved air-pressure sprayer structure wherein a spray mouthpiece unit, jointed to a cover unit via a pivot body, can be moved upwards and downwards to point at different directions for use. Besides, a set of loose-proof bolt and nut is applied to prevent the leak of water.

DETAILED DESCRIPTION OF THE PREFERRED EMBODIMENTS

Figure 1:
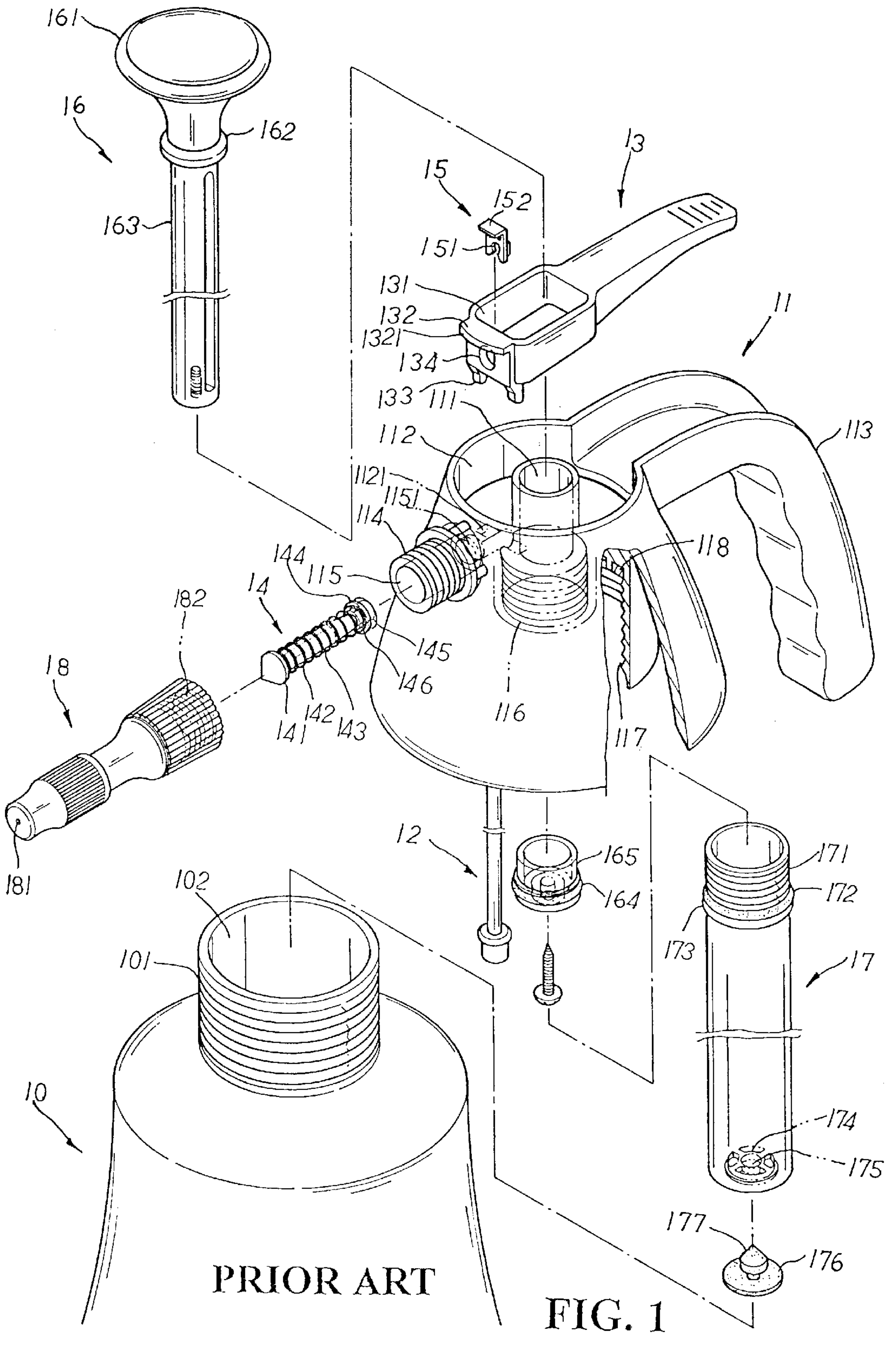
FIG. 1 is a perspective exploded view of a conventional air-pressure sprayer.
Figure 2:
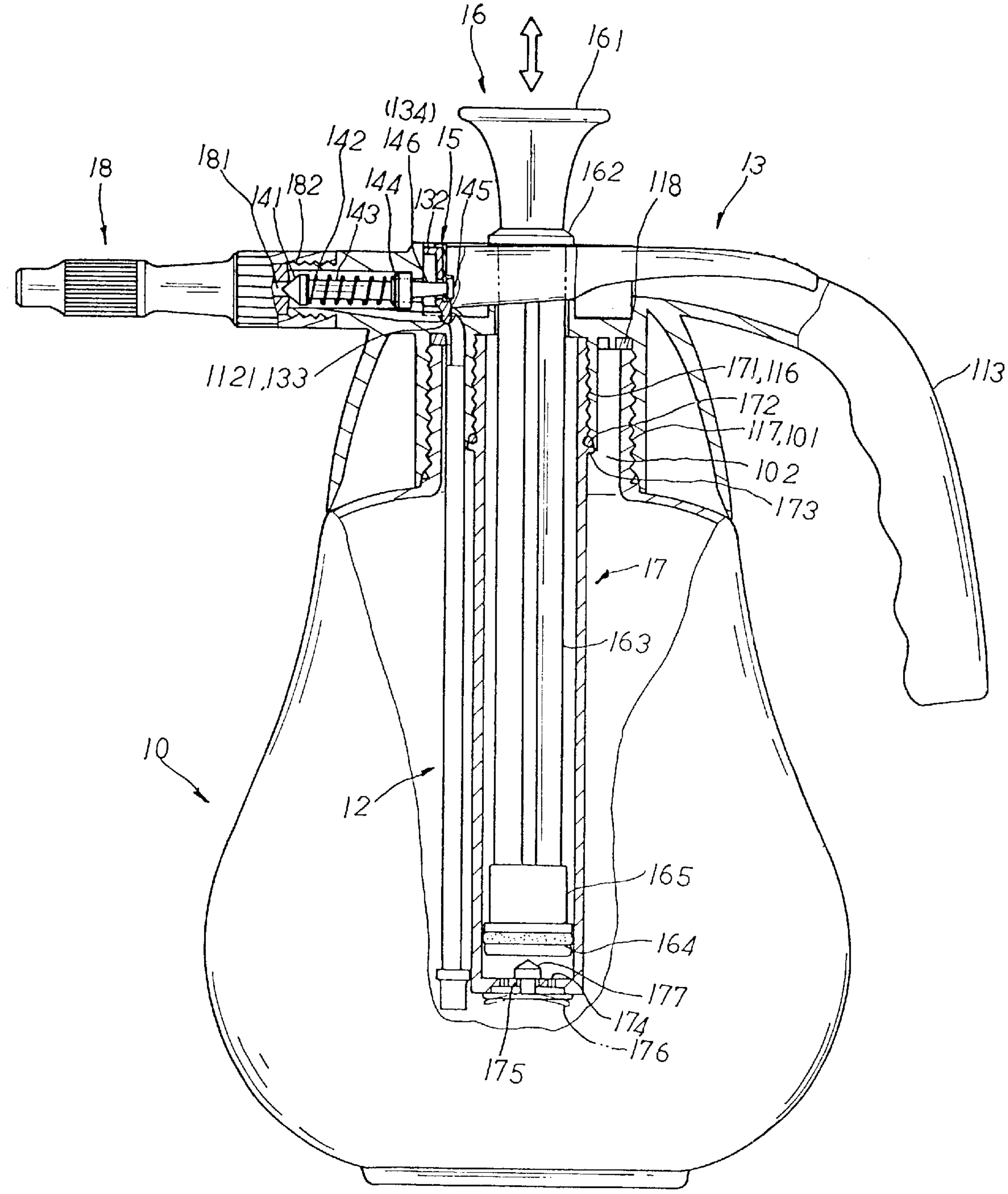
FIG. 2 PRIOR ART
FIG. 2 is a sectional view of a conventional air-pressure sprayer in operation.
Figure 3:
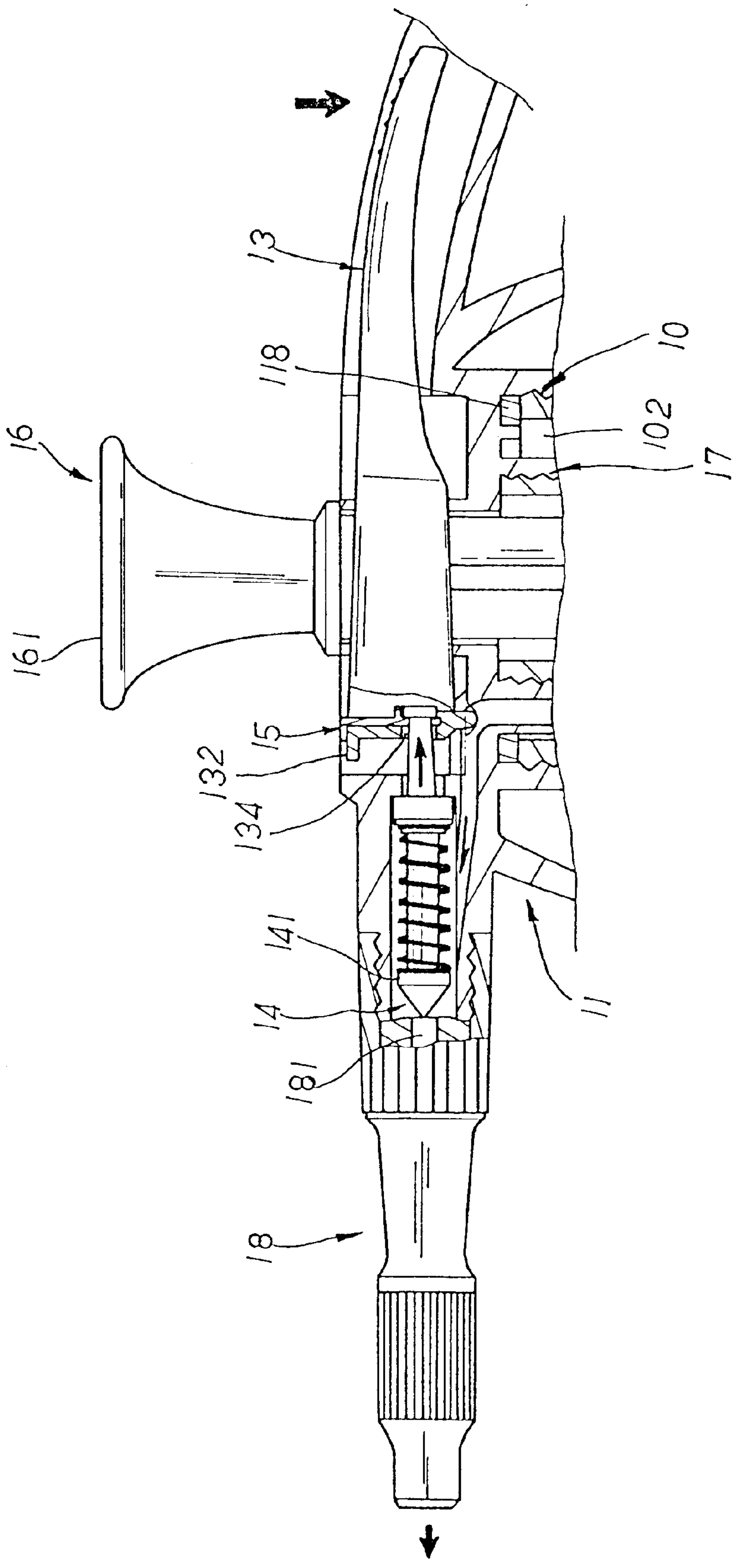
FIG. 3 PRIOR ART
FIG. 3 is a partially sectional view showing the press-and-pull movement of a conventional air-pressure sprayer in operation.
Figure 4:
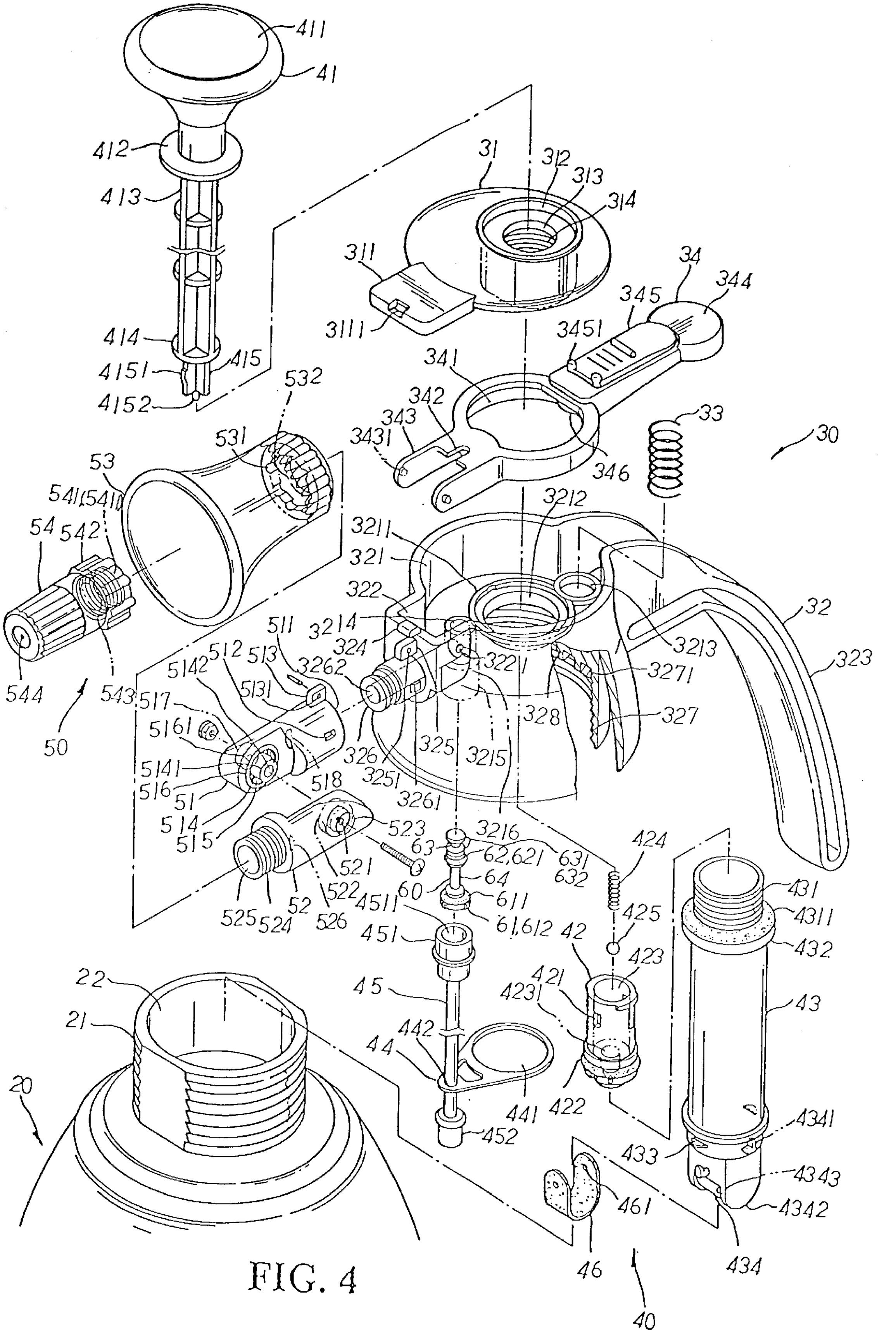
FIG. 4 is a perspective exploded view of the present invention.

Please refer to FIG. 4. The present invention is related to an improved air-pressure sprayer structure, comprising a container 20, a cover unit 30, an air-pump unit 40, a sprayer mouthpiece unit 50, and a water-stop valve 60. The container 20 is provided with a water-intake opening 22 and external threads 21 disposed at the upper section.

The cover unit 30 comprises an engaging body 31, a cover body 32, a spring 33, and a press body 34. The engaging body 31 is provided with a mounting means 311 projecting at one side thereof with a fixing hole 3111 disposed at the front of said mounting means 311 thereon, and a bearing seat 312 disposed at the other side with a pivot hole 313 disposed in the center thereof. A screw hole 314 is projected downwards inside said bearing seat 312 thereof. The cover body 32 is provided with an indented groove 321 at the top face thereof to hold said press body 34 thereof, an abutting means 322 projected at one side thereof, a handle bent downwards at the other side thereof, and a through hole 3212 circled by a fixing flanged ring 3211 disposed at the central top face thereof A first spring seat 3213 is disposed at one side of said fixing flanged ring 3211 thereof to receive said spring 33, and a projected hollow tube 3214 is disposed at the other side thereof, extending downwards to communicate with a sleeve pipe 3215 with a stop flange 3216 projected therebetween said hollow tube 3214 and said sleeve pipe 3215 thereof.

The abutting means 322 thereof is provided with a pair of corresponding through holes 3221 disposed at both lateral sides thereof, and a fixing block 324 projected at the front top thereof. A first fixing plate 325 having a first through hole 3251 disposed thereon is vertically disposed under said fixing block 324 at the front of said abutting means 322 thereof. A coupling means 326 having a pair of corresponding fixing keys 3261 disposed at both lateral sides and a water-outlet hole 3262 disposed at the center thereof is projected at the front of said abutting means 322. An internal screw hole 327 having an anti-leak washer 3271 and a projected ring seat 328 disposed thereon is projected downwards at the underside of said cover body 32 thereof. The press body 34 comprises a slot 341 of proper size disposed at the middle section thereof, an engaging recess 342 disposed at one side of said slot 341 thereof, and a press section 344 disposed at the other side thereof wherein a pair of corresponding locating plates 343, each having a locating block 3431 disposed thereon, are extended in parallel at both sides of said engaging recess 342, and a slide block 345 having a pair of locating posts 3451 disposed at one end thereof is provided at said press section 344 to be moved back and forth for location. The underside of said press body 34 is disposed a second spring seat 346 corresponding to the first spring seat 3213 thereof.

The air-pump unit 40 comprises a valve rod 41, an air-relief valve 42, a sleeve cylinder 43, a locating seat 44, an air-intake pipe 45, and a valve guard member 46. The valve rod 41 is provided with a head knob 411 extended at the top thereof, a locating piece 412 disposed at the proper section thereof, and a rod body 413 extending downwards at the lower section thereof. The rod body 413 is provided with a stop flange 414 projecting at the lower section thereof, a fitting body 415 extending under said stop flange 414 thereof, and a post 4152 disposed at the bottom thereof. The fitting body 415 is provided with a pair of fitting blocks 4151 projected at both corresponding sides thereof. The air-relief valve 42 comprises a pair of corresponding fitting holes 421 disposed at the proper location thereof, an anti-leak ring 422 disposed at the lower section thereof, a hollow column 423 defined at the interior thereof, and an air port 4231 disposed at the bottom of said hollow column 423 thereof wherein said air port 4231 is matched to a spring 424 and a ball 425.

The upper section of the sleeve cylinder 43 is provided with external threads 431, an anti-leak ring 4311 and a projecting flange 432, while the lower section thereof has a locating means 433 with a sleeve part 434 extended at the end thereof. Said sleeve part 434 is provided with an air outlet 4343 defined by a pair of protecting arms 4342 disposed at both lateral sides thereof, and a pair of corresponding hook blocks 4341 disposed at the top of said air outlet 4343 thereof. The locating seat 44 is made up of a large and a small sleeve slots 441, 442. One end of the air in-take pipe 45 is provided with a sleeve joint 451 having a water port 4511 disposed at the center thereof, and the other end thereof has a filter body 452. Said valve guard member 46, semi-oval in shape, is provided with a pair of corresponding hook holes 461 disposed in parallel at both arms thereof.

The spray mouthpiece unit 50 comprises a sleeve body 51, a pivot body 52, a shade body 53, and a spray nozzle 54. The sleeve body 51 is provided with a coupling hole 511 disposed at one end thereof, a pair of corresponding fixing holes 512 disposed at both sides thereof, and a second fixing plate 513 having a second through hole 5131 projecting on top of said coupling hole 511 thereof A pivoting column 514 having an anti-leak ring 5141 and a first pivoting hole 5142 disposed thereon is projected at one lateral side of said sleeve body 51 thereof, defining out one side of a water-outlet groove 515 disposed at the interior sleeve body 51. The other side of said water-outlet groove 515 is defined by a groove seat 516 having a anti-leak washer 5161 disposed thereon. The opposite end of said groove seat 516 is defined a water-inlet chamber 517, while the bottom of said coupling hole thereof is provided with a water-outlet port 518. The pivot body 52 is provided with a second pivot hole 521 disposed at one lateral side thereof, defining a water-outlet chamber 522 disposed at one side thereof and a water-inlet chamber 523 disposed at the opposite side of said water-outlet chamber 522 thereof. One end of said pivot body 52 is provided with an engaging hollow pipe 525 with external threads 524 disposed thereon and a water-discharge outlet 526 disposed at the interior of said pivot body 52. The shade body 53 has a multiple of internal indented grooves 531 defining the interior side, and a smaller sleeve hole 532 disposed at one end thereof. The spray nozzle 54 is provided with an anti-leak ring 541 land internal threads 541 disposed at one end, and a spray head 543 disposed at the other end thereof wherein a multiple of external fixing ribs 542 are disposed at the outer surface of said internal threads 541 at one end thereof, while a water-discharge port 544 is disposed at the center of said spray head 543 at the other end thereof.

The water-stop valve 60 is made up of a water-stop part 61 with an anti-leak ring 611 disposed at one end, an anti-leak part 62with a washer 621 disposed at the other end, and a water-outlet part 64 disposed between said water-stop part 61 and anti-leak part 62 thereof. A multiple of projecting blocks 612 are disposed at the outer surface of said water-stop part 61 thereof, and an engaging post 63 defined at both ends by a pair of parallel stop pieces 631, 632 is disposed on top of said anti-leak part 62 thereof.

Figure 5:
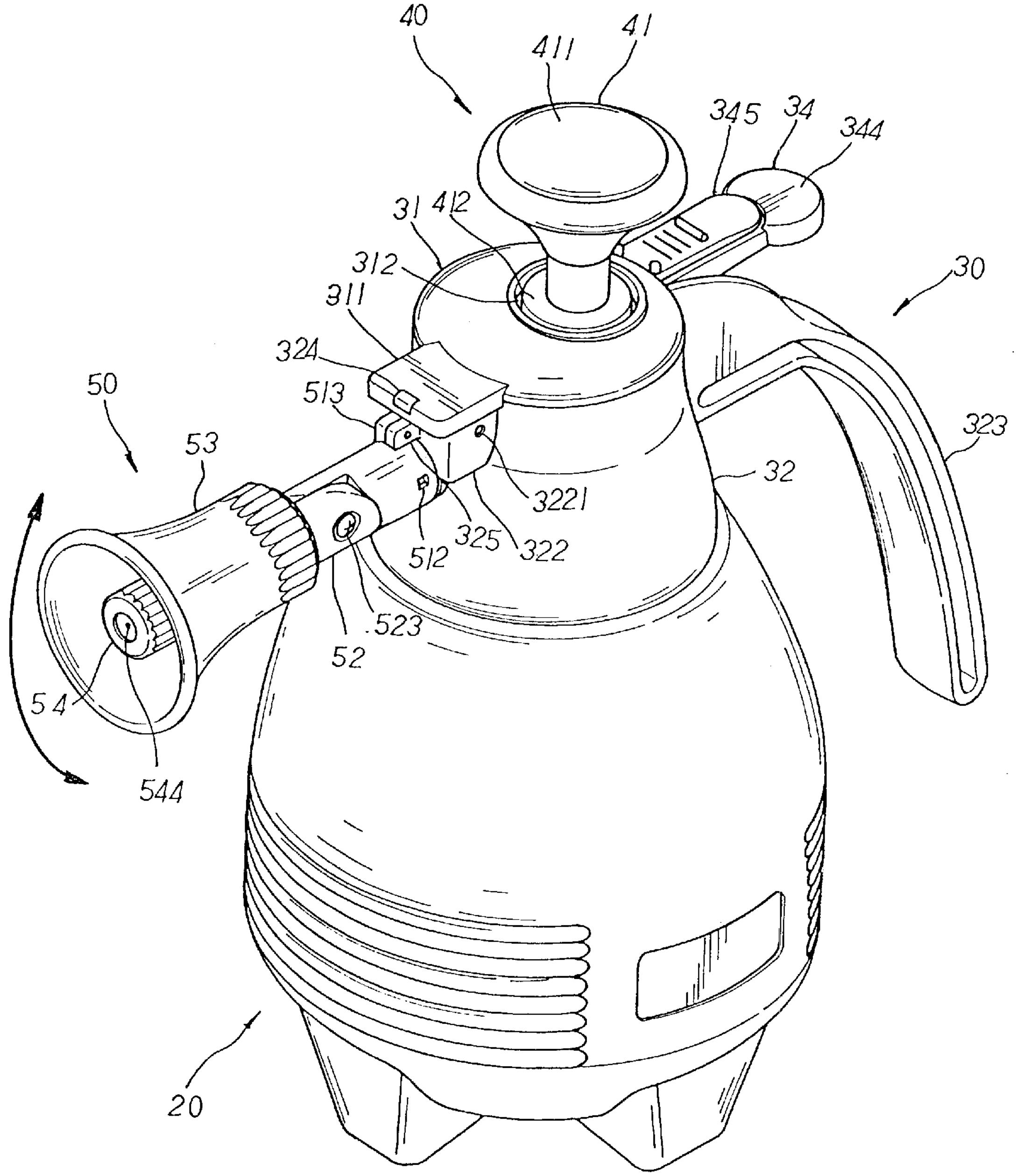
FIG. 5 is a perspective view of the present invention in assembly.
Figure 6:
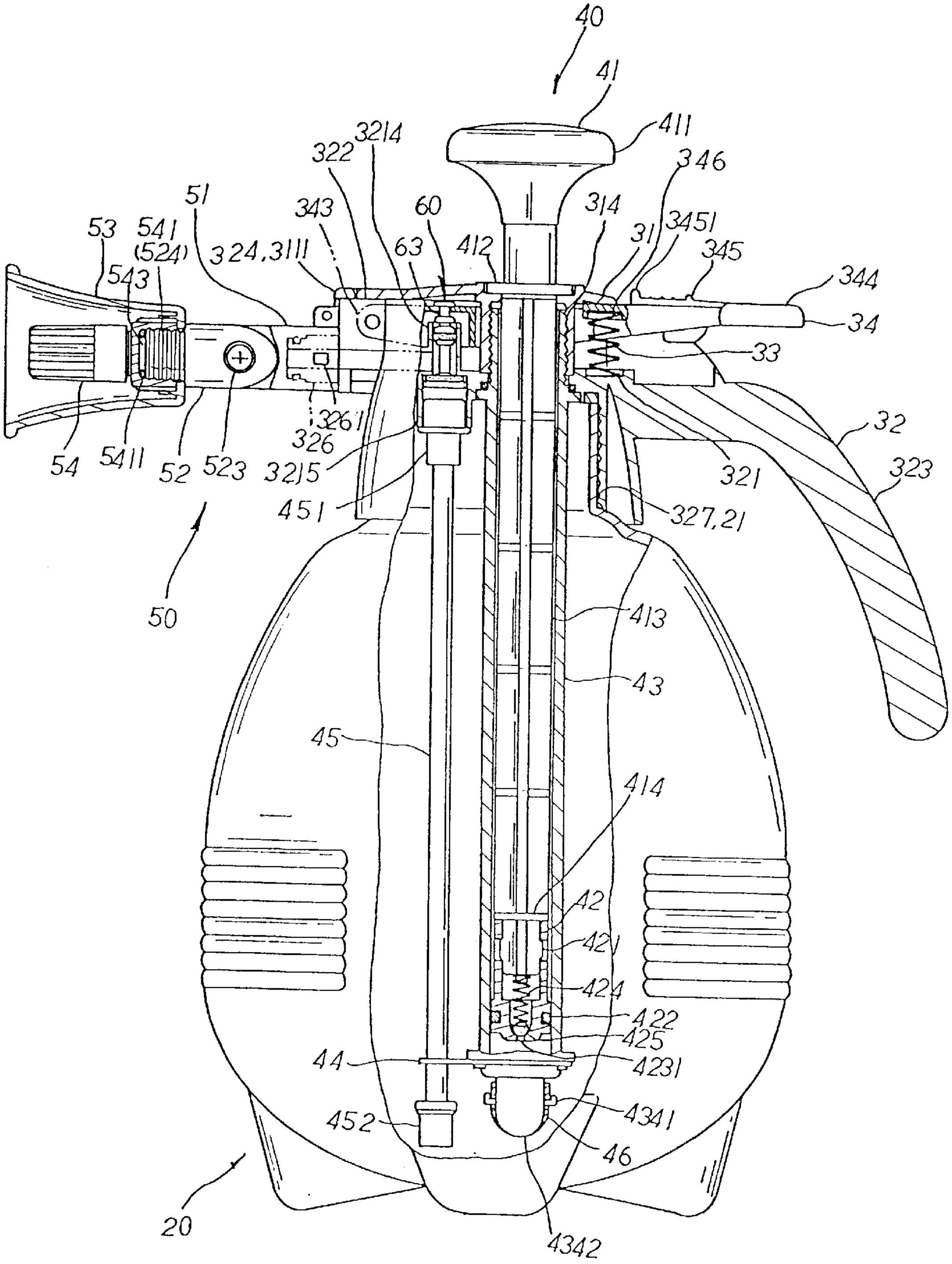
FIG. 6 is a sectional view of the present invention in assembly.

Please refer to FIGS. 5, 6. In assembly, the water-stop valve 60 is led through the sleeve pipe 3215 to come out of the hollow tube 3214 of said cover body 32 thereof a one end. The engaging recess 342 of said press body 34 is then matched to the engaging post 63 of said water-stop valve 60 and both locating blocks 3431 of said locating plates 343 thereof are inserted to the through holes 3221 of the abutting means 322, thus having said engaging recess 342 securely attached to said engaging post 63 defined both stop pieces 631, 632 thereof. The spring 33 is then located between the first and second spring seats 3213, 346 thereof, and the fixing block 324 at front top of the abutting means 322 thereof is inserted to the fixing hole 3111 of the mounting means 311, having said mounting means 311 abutted against said abutting means 322 and thus said engaging body 31 fixedly mounted on top of said cover body 32 thereof. The rod body 413 of said valve rod 41 is consecutively led through the pivot hole 313, the slot 341, and the through hole 3212 respectively to come out at one end till the locating piece 412 thereof is placed onto the bearing seat 312 thereof at the other end. The spring 424 is sleeve jointed to the post 4152 thereof and the ball 425 is placed onto the air port 4231 thereof. The fitting body 415 disposed at one end of said valve rod 41 thereof is then received to the hollow column 423 of said air-relief valve 42 with the fitting blocks 4151 thereof inserted into the fitting holes 421 thereof. The valve rod 41 engaged with said air-relief valve 42 at one end thereof is then led through the sleeve cylinder 43 from the end of said sleeve cylinder 43 provided with external threads 431. Said external threads 431 thereof is screw jointed to the screw hole 314 of said engaging means 31 thereof. The hook holes 461 of the valve guard member 46 is engaged with the hook blocks 4341 disposed at the top of the air-outlet 4343 thereof, having said valve guard member 46 abutted against the protecting arms 4342 of said sleeve part 434 at both lateral sides thereof.

The locating seat 44 is then applied to join both the sleeve cylinder 43 and the air-intake pipe 45 with the locating means 433 of said sleeve cylinder 43 fixed to the large pivot slot 441 thereof and the lower section of said air-intake pipe 45 to the small pivot slot 442 thereof. The internal screw hole 327 of the cover body 32 thereof is screw joined to the external threads 21 of the container 20, having said cover unit 30 mounted onto said container 20, and one end of said air-pump unit 40 engaged with said cover unit 30 led through the water-intake opening 22 and accommodated there-within said container 20 thereof The coupling hole 511 of the sleeve body 51 thereof is then engaged with the coupling means 326 of the cover body 32 thereof, having the fixing keys 3261 of the coupling means 326 thereof inserted to the fixing holes 512 of the sleeve body 51 thereof and the first and second fixing plates 325, 513 thereof abutted and securely attached via a pin passing through the first and second through holes 3251, 5131 thereof The sleeve body 51 is attached to the pivot body 52 via a bolt led through the second and first pivot holes 521, 5142 thereof respectively and pivot jointed said pivot body 52 to the pivot column 514 of said sleeve body 51 thereof by a nut. The external fixing ribs 542 of the spray nozzle 54 are engaged with the internal indented grooves 531 of the shade body 53 thereof; the engaging hollow pipe 525 of the pivot body 52 thereof is led through the smaller sleeve hole 532 of said shade body 53 and attached said pivot body 52 lo said spray nozzle 54 via the external threads 524 thereof screw jointed to the internal threads 541 thereof. Said spray nozzle 54 engaged with said shade body 53 can be moved upwards or downwards to point at different directions easily via said pivot body 52 thereof to complete the assembly of the present invention is shown in FIGS. 5, 6.

Figure 7:
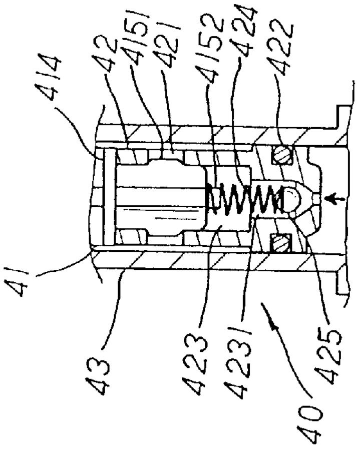
FIG. 7 is a partially sectional view of the air-pump unit of the present invention in operation.
Figure 8:
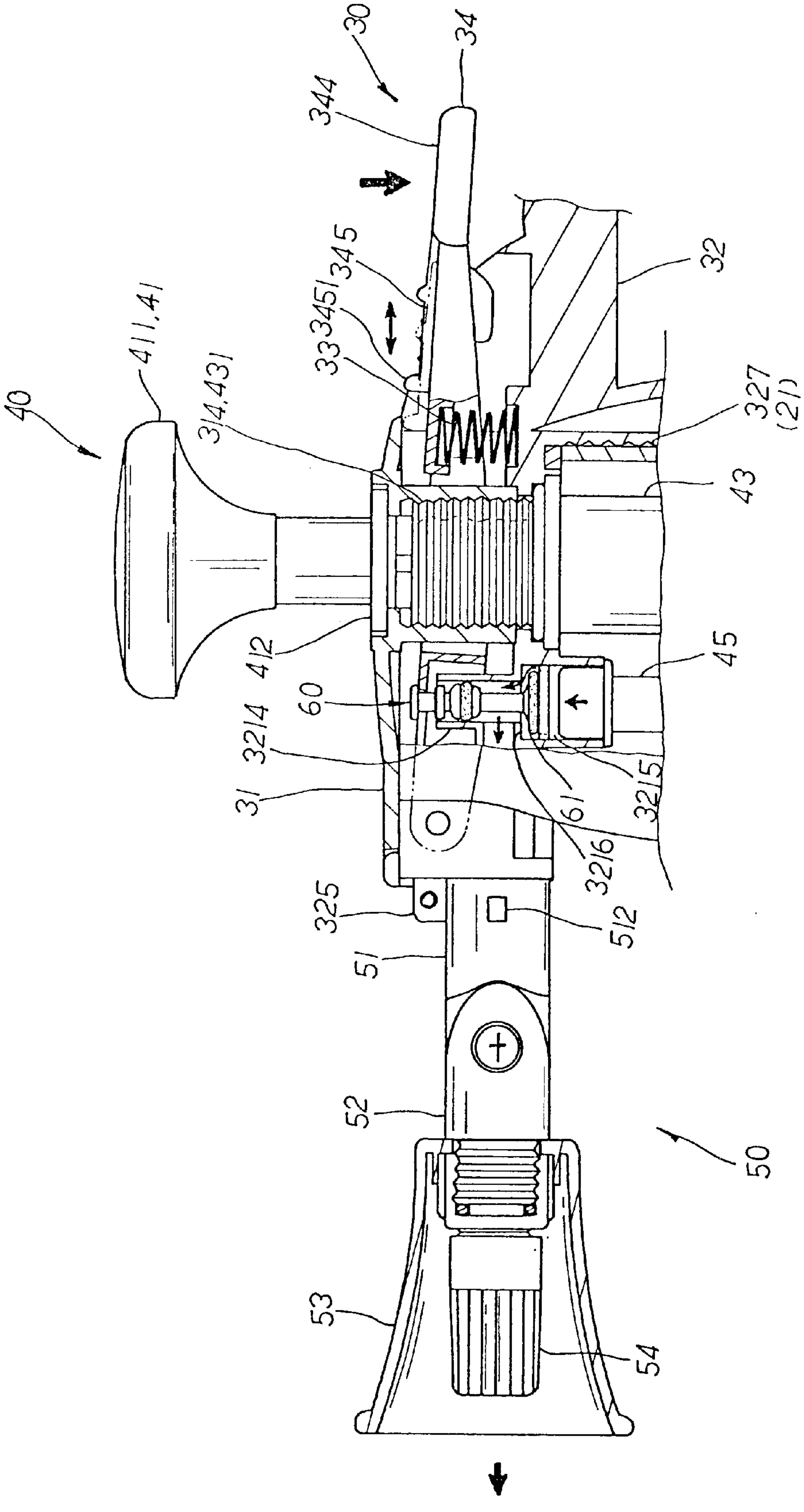
FIG. 8 is a partially sectional view showing the mechanism of the preset invention in pressing movement.

Please refer to FIGS. 7, 8. In operation, water is poured into said container 20 through said water-intake opening 22 thereof. Said head knob 411 of said valve rod 41 is moved up and down to pump air into said container 20. When said container 20 is saturated with air, said ball 425 placed within said air-relief valve 42 will be dislocated from said air port 4231, pushing upwards at said spring 424 and making the extra air released from said air port 4231 as shown in FIG. 7. In this way, said container 20 can avoid the danger of explosion due to over air-pressure. When said container 20 is loaded with air pressure, said press section 344 of said press body 34 is pushed downwards, compressing said spring 33 between said first and second spring seats 3213, 346 thereof and thus bringing down said water-stop valve 60 engaged with said press body 34 via said engaging recess 342 so as to release the air from said container 20. Meanwhile, the water brought out by the released air from said container 20 through said air-intake pipe 45 will flow through the water-outlet part 64 thereof to come out at said spray nozzle 54 thereof. Said slide block 345 of said press section 344 thereof can be moved forwards to have said locating posts 3451 thereof abutted against said engaging body 31 thereof for the constant outflow of water through said spray nozzle 54 without interruption as shown in FIG. 9.

Figure 9:
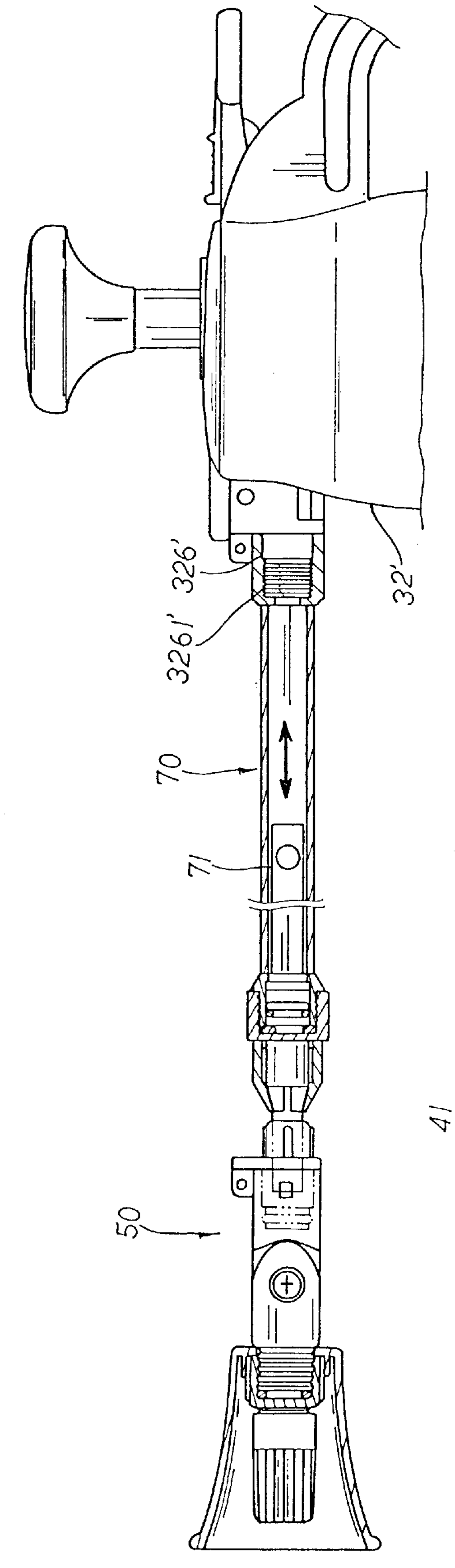
FIG. 9 is a diagram showing another embodiment of the present invention in assembly.

Please refer to FIG. 9 showing another embodiment of the present invention in assembly. A coupling means 326' of a cover body 32' is provided with external screw section 3261' to which an extensible sleeve body 71 having an inner tube 71 disposed therein is screw jointed at one end. The other end of said extensible sleeve body 71 is engaged with movable spray mouthpiece 50.

What is claimed is:

1. An air-pressure sprayer structure, comprising:

a container, a cover unit, an air-pump unit, a spray mouthpiece unit, and a water-stop valve wherein said container is provided with a water-inlet opening and external threads at an upper section thereof;

said cover unit, joined to said container via said external threads thereof, has a press body disposed at an upstream thereof which can control movement of said water-stop valve disposed in a sleeve pipe;

said air-pump unit, accommodated within said container, comprises a valve rod having a head knob extending out of said cover unit at a top thereof, and an air- relief valve disposed at an end thereof wherein said engaged valve rod and air-relief valve are led and joined to a sleeve cylinder;

said spray mouthpiece unit, attached to said cover unit at a downstream side thereof, can be moved upwards or downwards to point at different directions for use;

whereby, said press body having a slide block can be located for constant discharge of water out of said spray mouthpiece without interruption; and the force applied onto said press body being in parallel with a longitudinal axis of said water-stop valve thereof, allowing a balance of forces in operation and effectively preventing the distortion of said water-stop valve and thus a leak of both air and water from said container.

2. The air-pressure sprayer structure as claimed in claim 1, wherein said cover unit comprises an engaging body, a press body, a spring, and a cover body; said engaging body is joined to said cover body via a mounting means which is provided with a fixing hole to be engaged with a fixing block of an abutting of said cover body thereof; said press body is located between said engaging body and said cover body, having said spring sandwiched there-between said press body and said cover body thereof; a press section is disposed at one side of said press body wherein said press section has a slide block with locating posts disposed thereon to pushed back and forth for location.

3. The air-pressure sprayer structure as claimed in claim 1, wherein said air-pump unit comprises a valve rod, an air-relief valve, a sleeve cylinder, a locating seat, an air-intake pipe, and a valve guard member; said valve rod having a head knob extending out of said cover unit at the top thereof, and a rod body extending downwards to be engaged with said air-relief valve at the end thereof; said air-relief valve, having a spring and a ball disposed therein, and said rod body thereof is led and placed within said sleeve cylinder wherein said sleeve cylinder is provided with a sleeve part at the bottom to which said valve guard member is attached; said locating seat having one large and one small pivot slots disposed thereon is applied to joint both said air-intake pipe and said sleeve cylinder at the lower section thereof.

4. The air-pressure sprayer structure as claimed in claim 1, wherein said spray mouthpiece unit comprises a sleeve body, a pivot body, a shade body, and a spray nozzle; one end of said sleeve body is provided with a coupling hole having a pair of fixing holes disposed at both sides thereon, and one lateral side of said sleeve body is a pivoting column with a first pivot hole disposed therein corresponding to a second pivot hole disposed at one lateral side of said pivot body so as to pivot joint both said sleeve body and pivot body via an anti-loose bolt and nut; said pivot body having external thread disposed at one end so as to be engaged with said shade body and said spray nozzle for use.

* * * * *